US00PP13409P2

(12) United States Plant Patent
Sekiguchi

(10) Patent No.: US PP13,409 P2
(45) Date of Patent: Dec. 24, 2002

(54) OSTEOSPERMUM PLANT NAMED 'SEIKIMORA'

(76) Inventor: Masayuki Sekiguchi, 497 Kita-shiroda-cho, Maebashi-shi, Gunma-ken (JP)

( * ) Notice: Subject to any disclaimer, the term of this patent is extended or adjusted under 35 U.S.C. 154(b) by 0 days.

(21) Appl. No.: 09/996,364

(22) Filed: Nov. 30, 2001

(51) Int. Cl.[7] ..... A01H 5/00

(52) U.S. Cl. ..... Plt./360
(58) Field of Search ..... Plt./360

*Primary Examiner*—Bruce R. Campell
*Assistant Examiner*—Annette Para
(74) *Attorney, Agent, or Firm*—C. A. Whealy

(57) ABSTRACT

A distinct cultivar of Osteospermum plant named 'Seikimora', characterized by its uniformly mounded and outwardly spreading plant habit; freely branching growth habit; freely flowering habit; and orange-colored ray florets and dark purple-tipped disc florets.

1 Drawing Sheet

BOTANICAL CLASSIFICATION/CULTIVAR DESIGNATION

*Osteospermum ecklonis* cultivar Seikimora.

BACKGROUND OF THE INVENTION

The present Invention relates to a new and distinct cultivar of Osteospermum plant, botanically known as *Osteospermum ecklonis*, and hereinafter referred to by the name 'Seikimora'.

The new Osteospermum is a product of a planned breeding program conducted by the Inventor in Gunma-den, Japan. The objective of the breeding program is to create new Osteospermum cultivars with interesting floret colors.

The new Osteospermum was discovered as a naturally-occurring whole plant mutation of the *Osteospermum ecklonis* cultivar Seikilrem, U.S. Plant Patent application filed concurrently.

The new Osteospermum was discovered and selected by the Inventor in April, 1996, as a single flowering plant within a population of plants of the parent cultivar in a controlled environment in Gunma-den, Japan.

Asexual reproduction of the new Osteospermum by terminal vegetative cuttings was first conducted in Gunma-den, Japan on Jun. 1, 1996. Asexual reproduction by cuttings has shown that the unique features of this new Osteospermum are stable and reproduced true to type in successive generations.

SUMMARY OF THE INVENTION

The cultivar Seikimora has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Seikimora'. These characteristics in combination distinguish 'Seikimora' as a new and distinct Osteospermum:

1. Compact, mounded and outwardly spreading plant habit.

2. Freely branching growth habit.

3. Freely flowering habit.

4. Orange-colored ray florets and dark purple-tipped disc florets.

Plants of the new Osteospermum differ primarily from plants of the parent, the cultivar Seikilrem, in ray floret coloration.

Plants of the new Osteospermum can be compared to plants of the cultivar Akope, disclosed in U.S. Plant patent application Ser. No. 09/722,804. However, plants of the new Osteospermum are not as vigorous and have smaller inflorescences than plants of the cultivar Akope. In addition, plants of the new Osteospermum and the cultivar Akope differ in floret coloration.

BRIEF DESCRIPTION OF THE PHOTOGRAPHS

The accompanying colored photographs illustrate the overall appearance of the new Osteospermum showing the colors as true as it is reasonably possible to obtain in colored reproductions of this type. Colors in the photographs may differ from the color values cited in the detailed botanical description which accurately describe the colors of the new Osteospermum.

The photograph at the top of the sheet comprises a side perspective view of three typical flowering plants of 'Seikimora' grown in a 22-cm container.

The photograph at the bottom of the sheet is a close-up view of typical developing inflorescence buds, upper and lower surfaces of typical fully opened inflorescences, and upper surfaces of typical leaves of 'Seikimora'.

DETAILED BOTANICAL DESCRIPTION

The aforementioned photographs and following observations and measurements describe plants grown in Bonsall, Calif., in an outdoor nursery during the late spring and early summer under full sun conditions with day temperatures ranging from 18 to 35° C. and night temperatures ranging from 4 to 18° C. After planting rooted cuttings, plants were grown for about eight weeks in 22-cm containers with three plants per container and were pinched one time. Color references are made to The Royal Horticultural Society Colour Chart, 1995 edition, except where general terms of ordinary dictionary significance are used.

Botanical classification: *Osteospermum ecklonis* cultivar Seikimora.

Parentage: Naturally-occurring whole plant mutation of the *Osteospermum ecklonis* cultivar Seikilrem, U.S. Plant Patent application filed concurrently.

Propagation:

*Type.*—Terminal vegetative cuttings.

*Time to initiate rooting.*—Summer: About 12 days at 25° C. Winter: About 20 days at 15° C.

*Time to develop roots.*—Summer: About 20 days at 25° C. Winter: About 27 days at 15° C.

*Root description.*—Fine, fibrous and well-branched.

Plant description:

*Appearance.*—Perennial herbaceous container and garden plant. Compact and mounded plant habit; initially upright and then outwardly spreading. Freely branching, about six lateral branches develop after pinching; dense and full plants. Moderately vigorous growth habit.

*Plant height.*—About 22 cm.

*Plant width or area of spread.*—All three plants, about 20 cm; individual plants, about 12 cm.

*Lateral branches.*—Length: About 13 cm. Diameter: About 3 mm. Internode length: About 1 cm. Aspect: Upright to outward. Strength: Strong. Texture: Pubescent. Color: 144B.

*Foliage description.*—Arrangement: Alternate; simple. Number of leaves per lateral branch: About 12. Length: About 3.25 cm. Width: About 1.4 cm. Shape: Elliptic, strap-like. Apex: Acute. Base: Attenuate. Margin: Entire with occasional tiny serrations. Venation pattern: Pinnate. Texture: Smooth, glabrous. Color: Young foliage, upper and lower surfaces: 144A. Fully expanded foliage, upper surface: 147A. Fully expanded foliage, lower surface: 147B. Venation, upper surface: 144C. Venation, lower surface: 147C. Petiole: Length: About 1.25 cm. Diameter: About 4 mm. Texture, upper and lower surfaces: Glabrous. Color, upper and lower surfaces: 144C.

Inflorescence description:

*Appearance.*—Terminal and axillary inflorescences held above and beyond the foliage on moderately strong peduncles. Composite inflorescence form, radially symmetrical, with ligulate-shaped ray florets and disc florets massed at the center; ray and disc florets arranged acropetally on a capitulum. Inflorescences persistent. Inflorescences face upright or outward.

*Flowering response.*—Plants flower continuous and freely from the spring through the fall.

*Postproduction longevity.*—Inflorescences maintain good color and substance for about one week on the plant when grown in an outdoor environment.

*Quantity of inflorescences.*—Freely flowering; at one time, about five open inflorescences and inflorescence buds per lateral stem.

*Fragrance.*—None detected.

*Inflorescence bud* (*at stage of showing color*).—Length: About 1.4 cm. Diameter: About 7 mm. Shape: Ovoid. Color, ray florets, lower or outer surface: 22A.

*Inflorescence size.*—Diameter: About 4 cm. Depth (height): About 1.5 cm. Disc diameter: About 7 mm.

*Ray florets.*—Length: About 2 cm. Width: About 4 mm. Shape: Ligulate. Apex: Slightly emarginate. Base: Acute. Margin: Entire. Texture: Velvety. Orientation: Initially upright then about 50 to 55° from vertical. Number of ray florets per inflorescence: About 18 in a single whorl. Color: When opening, upper surface: 24A. When opening, lower surface: Ground color, 24B; central stripe, 194D. Fully opened, upper surface: At apex, 24A; mid-section 24A to 24B; towards base, a white, 155D, band; below white band, a band of purple, 79B; main color does not fade with subsequent development. Fully opened, lower surface: Ground color, 24B to 24C, overlain with faint central stripe, close to 194D.

*Disc florets.*—Shape: Tubular, elongated. Apex: Five-pointed. Length: About 7 mm. Width: At apex: About 1 mm. At base: Less than 1 mm. Number of disc florets per inflorescence: About 50. Color, immature and mature: 155D; apex, 79A.

*Phyllaries.*—Length: About 1 cm. Diameter: About 1 mm. Shape: Linear. Apex: Narrowly acute. Base: Fused. Margin: Entire. Texture: Coarse, pubescent. Number per inflorescence: About 16 in a single whorl. Color: Upper surface: 146A. Lower surface: 146C.

*Peduncles.*—Length, terminal peduncle: About 6 cm. Length, second peduncle: About 3.5 cm. Length, third penduncle: About 3.2 cm. Diameter: About 1.5 mm. Angle: Terminal peduncles, erect; secondary and tertiary peduncles, about 45° from vertical. Strength: Moderately strong. Texture: Smooth. Color: 144A.

*Reproductive organs.*—Androecium: Present on disc florets only. Stamen number: Five per floret; fused around style. Anther shape: Oblong. Anther length: About 1 mm. Anther color: 79B to 79C. Pollen amount: Scarce. Pollen color: 23A. Gynoecium: Present on both ray and disc florets. Pistil number: One per floret. Pistil length: About 6 mm. Stigma shape: Two-parted. Stigma color: 77A. Style length: About 5 mm. Style color: 155D. Ovary color: 145C.

*Seed/fruit.*—Seed and/or fruit production has not been observed.

Disease/pest resistance: Resistance to pathogens and pests common to Osteospermums has not been observed on plants grown under commercial greenhouse or outdoor conditions.

Temperature tolerance: Plants of the new Osteospermum have been observed to tolerate temperatures from 4 to 35° C.

It is claimed:

1. A new and distinct cultivar of Osteospermum plant named 'Seikimora', as illustrated and described.

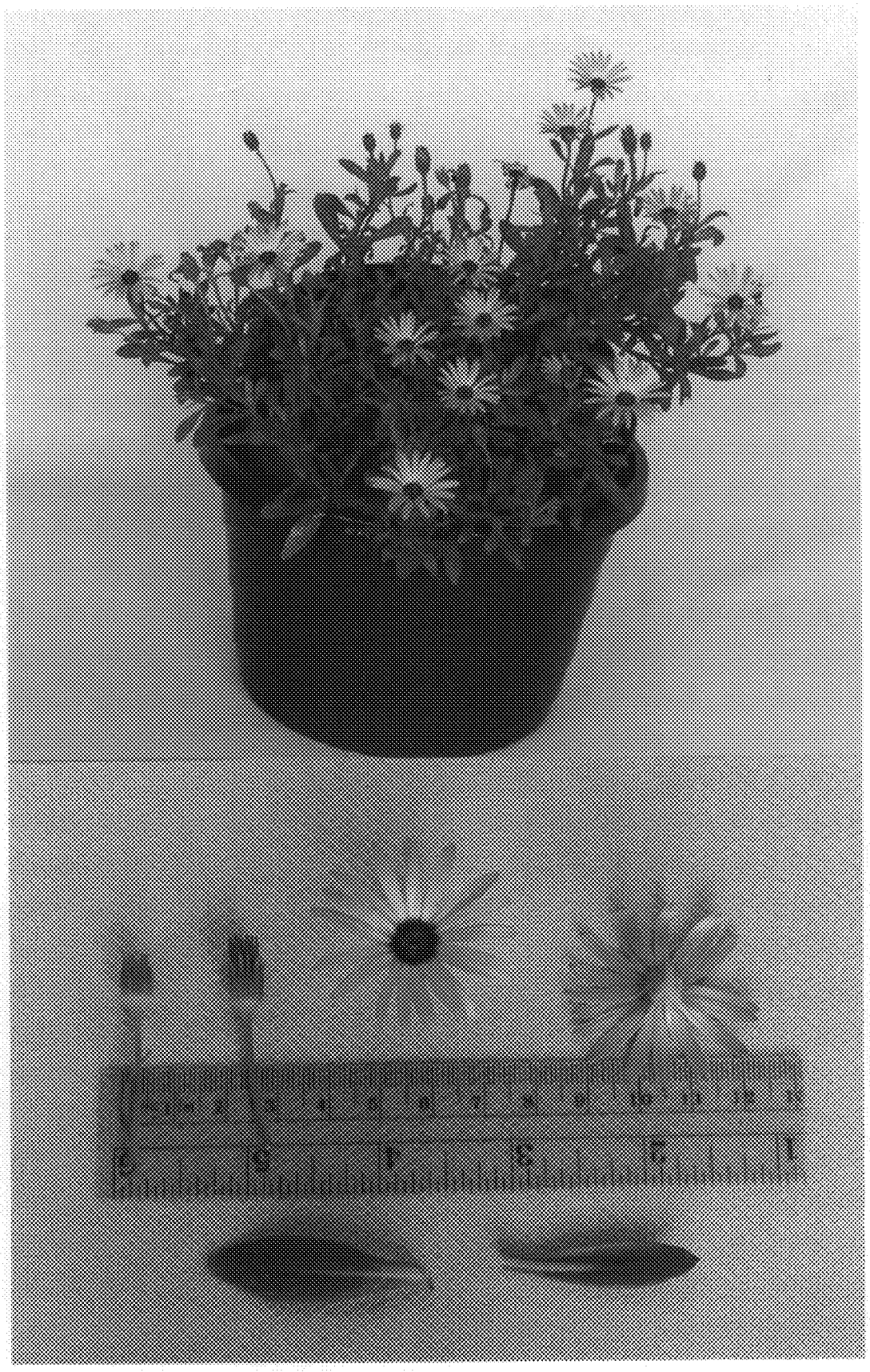

* * * * *